(12) United States Patent
Delanghe et al.

(10) Patent No.: US 12,029,552 B2
(45) Date of Patent: Jul. 9, 2024

(54) DIRECT INFRARED ANALYSIS OF POST-TRANSLATIONAL MODIFICATION OF PROTEINS

(71) Applicant: UNIVERSITEIT GENT, Ghent (BE)

(72) Inventors: Joris Delanghe, Aalst (BE); Marijn Speeckaert, Waasmunster (BE); Tinne Monteyne, Melsen (BE); Thomas De Beer, Bachte (BE)

(73) Assignee: UNIVERSITEIT GENT, Ghent (BE)

( * ) Notice: Subject to any disclaimer, the term of this patent is extended or adjusted under 35 U.S.C. 154(b) by 770 days.

(21) Appl. No.: 16/082,113

(22) PCT Filed: Mar. 6, 2017

(86) PCT No.: PCT/EP2017/055229
§ 371 (c)(1),
(2) Date: Sep. 4, 2018

(87) PCT Pub. No.: WO2017/153359
PCT Pub. Date: Sep. 14, 2017

(65) Prior Publication Data
US 2019/0117134 A1    Apr. 25, 2019

(30) Foreign Application Priority Data

Mar. 6, 2016 (EP) .................................... 16158854

(51) Int. Cl.
*A61B 5/145* (2006.01)
*A61B 5/00* (2006.01)
*G01N 21/35* (2014.01)

(52) U.S. Cl.
CPC ........ *A61B 5/14532* (2013.01); *A61B 5/0075* (2013.01); *A61B 5/4842* (2013.01);
(Continued)

(58) Field of Classification Search
CPC ............ A61B 5/44–449; A61B 5/0075; A61B 5/14532; A61B 5/4842
See application file for complete search history.

(56) References Cited

U.S. PATENT DOCUMENTS 7,043,288 B2    5/2006   Davis, III et al.
8,174,394 B2    5/2012   Ridder et al.
(Continued)

FOREIGN PATENT DOCUMENTS

CN       102365047 A    2/2012
JP       2005080710 A   3/2005
(Continued)

OTHER PUBLICATIONS

Coopman et al. "Glycation in human finger nail clipping using reflectance IR spectrometry, a new marker for diabetes diagnosis and monitoring" AACC 2015 Annual Meeting & Clinical Lab Expo, Poster Abstracts accepted for publication, Jul. 29, 2015 (Jul. 29, 2015), p. 0, 1. B-345, B-349, XP055296700 (Year: 2015).*
(Continued)

*Primary Examiner* — Keith M Raymond
*Assistant Examiner* — Milton Truong
(74) *Attorney, Agent, or Firm* — Workman Nydegger

(57) ABSTRACT

A method and system are provided for measuring post-translational modification of proteins in a subject. The method comprises recording of infrared radiation within a predetermined wavenumber range and attenuated by an integument of the subject, such that the integument is still attached to the subject. The method further comprises the step of comparing the attenuation of infrared radiation to a predetermined value for deriving information regarding post-translational modification of proteins in the integument.

13 Claims, 6 Drawing Sheets

(52) U.S. Cl.
CPC .......... *A61B 5/4848* (2013.01); *A61B 5/4866* (2013.01); *G01N 21/35* (2013.01)

(56) References Cited

U.S. PATENT DOCUMENTS

| | | | |
|---|---|---|---|
| 10,085,693 | B2 | 10/2018 | Yamanaka |
| 2003/0191378 | A1* | 10/2003 | Davis, III .............. A61B 5/0059 600/310 |
| 2005/0209514 | A1 | 9/2005 | Oshima et al. |
| 2007/0161877 | A1* | 7/2007 | Arai ..................... A61B 18/203 600/316 |
| 2009/0318814 | A1 | 12/2009 | Kuratsune et al. |
| 2010/0010325 | A1* | 1/2010 | Ridder ............... A61B 5/14546 600/310 |
| 2010/0185064 | A1* | 7/2010 | Bandic .................. A61B 5/415 600/306 |
| 2011/0282167 | A1 | 11/2011 | Ridder et al. |
| 2014/0155718 | A1* | 6/2014 | Kramer ................. A61B 5/449 600/344 |
| 2015/0208983 | A9 | 7/2015 | Ridder et al. |
| 2015/0305658 | A1* | 10/2015 | Islam ................... A61B 5/7257 433/27 |
| 2016/0022214 | A1 | 1/2016 | Yamanaka |

FOREIGN PATENT DOCUMENTS

| | | |
|---|---|---|
| JP | 2005521531 A | 7/2005 |
| JP | 2005321289 A | 11/2005 |
| JP | 2015154853 A | 8/2015 |
| UA | 19668 U | 12/2006 |
| UA | 21294 U | 3/2007 |
| WO | 2007066589 A1 | 5/2009 |

OTHER PUBLICATIONS

Kishabongo et al. "Glycated nail proteins: a new approach for detecting diabetes in developing countries". Tropical Medicine and International Health, vol. 19 No. 1 pp. 58-64 Jan. 2014 (Year: 2014).*

Jaisson et al. "Impact of Carbamylation on Type I Collagen Conformational Structure and Its Ability to Activate Human Polymorphonuclear Neutrophils", Chemistry & Biology 13, 149-159, Feb. 2006 (Year: 2006).*

Satoshi Yoshida, Makoto Yoshida, Mayumi Yamamoto, Jun Takeda, "Optical screening of diabetes mellitus using non-invasive Fourier-transform infrared spectroscopy technique for human lip". Journal of Pharmaceutical and Biomedical Analysis, vol. 76, pp. 169-176, 2013. (Year: 2013).*

Farhan, K.M. et al. "Comparative study on secondary structural changes in diabetic and non-diabetic human finger nail specimen by using FTIR spectra". Clinica Chimica Acta 412 (2011) 386-389 (Year: 2011).*

Egawa, M. et al. "Determining Water Content in Human Nails with a Portable Near-Infrared Spectrometer". Applied Spectroscopy. 2003;57(4):473-478 (Year: 2003).*

Herman, H.H. "Racial and Ethnic Differences in the Relationship between HbA1c and Blood Glucose: Implications for the Diagnosis of Diabetes". J Clin Endocrinol Metab, 2012, 97(4):1067-1072 (Year: 2012).*

Ansari et al., "Assessing Glycemic Control in Patients With Diabetes and End-Stage Renal Failure," American Journal of Kidney Disease, vol. 41, No. 3, Mar. 2003, pp. 523-531.

Berg et al., "Carbamylation of Serum Albumin as a Risk Factor for Mortality in Patients with Kidney Failure," Science Translational Medicine, vol. 5, No. 175, Mar. 6, 2013, 23 Pages.

Bisse et al., "Heterogeneity of Hemoglobin A1d: Assessment and Partial Characterization of Two New Minor Hemoglobins A1d3a and A1d3b, Increased in Uremic and Diabetic Patients, Respectively," Journal of Chromatography B, vol. 687, 1996, pp. 349-356.

Coopman et al., "Glycation in Human Finger Nail Clipping Using Reflectance IR Spectrometry, a New Marker for Diabetes Diagnosis and Monitoring," 2015 Annual Meeting & Clinical Lab Expo, Poster Abstracts Accepted for Presentation, Jul. 29, 2015, 4 Pages.

Katchunga et al., "Glycated Nail Proteins as a New Biomarker in Management of the South Kivu Congolese Diabetics," Biochemia Medica, vol. 25, No. 3, 2015, pp. 469-473.

Kishabongo et al., "Glycation of Nail Proteins: From Basic Biochemical Findings to a Representative Marker for Diabetic Glycation-Associated Target Organ Damage," PLOS One, vol. 10, No. 3, Mar. 17, 2015, 13 Pages.

Schnedl et al., "Glycated Hemoglobin and Liver Disease in Diabetes Mellitus," Wiener Medizinische Wochenschrift, vol. 155, No. 17, 2005, pp. 411-415.

Smith et al., "Carbamylated Haemoglobin in Chronic Renal Failure," Clinica Chimica Acta, vol. 178, 1988, pp. 297-304.

Wang et al., "Protein Carbamylation Links Inflammation, Smoking, Uremia and Atherogenesis," Nature Medicine, vol. 13, No. 10, Oct. 2007, pp. 1176-1184.

Extended European Search Report from EP Application No. 16158854. 6, Aug. 25, 2016.

International Search Report and Written Opinion from PCT Application No. PCT/EP2017/055229, Jun. 12, 2017.

Pogorelova et al., "Post-Translational Modification and Differential Expression Proteins in Placental Insufficiency," Reproduction Problems, vol. 6, as early as Jan. 1, 2016, 11 Pages.

Office Action from corresponding RU Application No. 2018134766/ 14, Apr. 9, 2020.

Smith et al., "Carbamylated Haemoglobin in Chronic Renal Failure," Clinica Chimica Acta, vol. 178, Sep. 25, 1988, pp. 297-304.

Coopman et al., Glycation in Human Finger Nail Clipping using Reflectance IR Spectrometry, a New Marker for Diabetes Diagnosis and Monitoring, AACC 2015 Annual Meeting & Clinical Lab EXPO, Jul. 26-30, 2015, 5 Pages.

Office Action from corresponding Japanese Application No. 2018-565461, Jan. 12, 2021.

Heise et al., "Recent Progress in Non-Invasive Diabetes Screening by Diffuse Reflectance Near-Infrared Skin Spectroscopy," Biomedical Vibrational Spectroscopy III: Advances in Research and Industry, vol. 6093, Feb. 27, 2006, 9 Pages.

Tura et al., "Non-Invasive Glucose Monitoring: Assessment of Technologies and Devices According to Quantitative Criteria," Diabetes Research and Clinical Practice, vol. 77, Dec. 1, 2006, pp. 16-40.

Office Action from corresponding European Application No. 17707935. 7, Oct. 12, 2021.

Search Report from corresponding Chinese Application No. 201780015122.X, Sep. 3, 2021.

Office Action from corresponding Chinese Application No. 201780015122.X, Sep. 9, 2021.

* cited by examiner

DIRECT INFRARED ANALYSIS OF POST-TRANSLATIONAL MODIFICATION OF PROTEINS

TECHNICAL FIELD OF THE INVENTION

The present invention relates to the measurement of post-translational modification of proteins in a subject and more specifically to the measurement of post-translational modification of proteins through the use of infrared spectroscopy, whereby the post-translational modification of proteins can be representative for a disease such as for example diabetes mellitus or renal insufficiency.

BACKGROUND OF THE INVENTION

Although the prevalence of diabetes mellitus is dramatically rising in sub-Saharan Africa, accurate diagnosis and monitoring of this metabolic disease by local health professionals is still problematic. According to the revised criteria of the American Diabetes Association, the European Association for the Study of Diabetes and the International Diabetes Federation, the diagnosis of diabetes mellitus is based on plasma glucose or hemoglobin A1c (HbA1c) concentrations. For plasma glucose concentrations, the diagnosis is made based on either a fasting plasma glucose concentration ≥126 mg/dL (7.0 mmol/L), a random plasma glucose concentration ≥200 mg/dL (11.1 mmol/L) or a 2-h plasma glucose value ≥200 mg/dL (11. mmol/L) in the 75 g oral glucose tolerance test (OGTT)]. For hemoglobin A1c (HbA1c), the diagnosis is based on a concentration ≥48 mmol/mol.

However, the use of these golden standards in sub-Saharan Africa is hampered for several reasons. Venous blood glucose, a widely used tool for diagnosing and monitoring of diabetic patients, is subject to preanalytical variation. The reported HbA1c results are influenced by the presence of hemoglobinopathies, iron deficiency, factors that influence red blood cell age and red blood cell survival, uremia and hyperbilirubinemia. Furthermore, a doctor or nurse is typically required to draw the blood samples. In addition, blood analyses are often refused by African patients due to cultural or religious objections.

It is also known that an increased carbamylation can be observed in patients with renal insufficiency. It is to be noted that many adverse health effects observed in terminal renal insufficiency (e.g. atherosclerosis, anemia) have been associated with the increased carbamylation. Up to now, nevertheless there are no clinically useful biomarkers available for assessing carbamylation which can be used in a routine clinical laboratory.

There is thus still a need within the art for cheap, fast, portable and accurate methods of measuring post-translational modification of proteins, such as glycation or carbamylation, within a subject, which do not rely on blood sampling.

SUMMARY OF THE INVENTION

It is an object of the present invention to provide good methods, systems and markers for post-translational modification of proteins within a subject. It is an advantage of the post-translational modification of proteins that these may provide information for diagnosis of diseases such as for example diabetes mellitus or renal insufficiency.

It is an advantage of embodiments of the present invention that post-translational modification of proteins, such as glycation or carbamylation, may be measured in a non-invasive way. In the case of glycation, the glycation may be an indirect measure for the mean glycemia in the blood.

It is an advantage of embodiments of the present invention that post-translational modification of proteins may be measured in a way that is cheap, fast and portable, while still being sufficiently accurate.

It is an advantage of embodiments of the present invention that, for the case where the post-translational modification of proteins is glycation of proteins, the glycated protein marker may reflect the glycation of the majority of the proteins related to target organ damage.

It is an advantage of embodiments of the present invention that an average post-translational modification of proteins of a longer period of time may be obtained in a single measurement.

It is an advantage of embodiments of the present invention that an evolution of the translational modification of proteins over a longer period of time may be obtained.

It is an advantage of embodiments of the present invention that, for the case where the post-translational modification of proteins is glycation of proteins, measurement of the glycation may be used to diagnose diabetes mellitus.

It is an advantage of embodiments of the present invention that, for the case where the post-translational modification of proteins is carbamylation of proteins, measurement of the carbamylation may be used to diagnose renal insufficiency.

The above objective is accomplished by a method, a system, a marker and a use according to the present invention.

In a first aspect, the present invention relates to a method for measuring post-translational modification of proteins in a subject, the method comprising recording of infrared radiation within a predetermined wavenumber range, attenuated by an integument of said subject, wherein said integument is still attached to said subject, and comparing said attenuation of infrared radiation to a predetermined value for deriving information regarding post-translational modification of proteins in the integument.

It was surprisingly found that attenuation of infrared radiation in specific wavenumber ranges allows for identifying post-translational modification of proteins, e.g. glycation or carbamylation, in integuments such as nails that have not been removed from the subject, e.g. human body. In other words, a non-invasive technique for detection of post-translational modification, e.g. glycation or carbamylation, of nail keratins is obtained. Since the measurement technique is based on infrared spectroscopy, it is an advantage of embodiments of the present invention that methods are provided for measuring post-translational modification that are cheap, fast and portable but still sufficiently accurate. As no blood sampling is required, no doctor or nurse is required for taking the test. It is an advantage of embodiments of the present invention that the method does not require nail clipping.

It is an advantage of some embodiments of the present invention wherein glycation is measured, that information can be obtained regarding fructosamines formed in the nail matrix. It is an advantage of such embodiments of the present invention that information regarding diabetes can be obtained for a subject.

The method may comprise irradiating the nail of the subject with said infrared radiation.

Said integument of said subject may be a nail of said subject.

Where said post-translational modification of proteins consists of glycation of nail keratins, the method comprises recording of infrared radiation from within the wavenumber range of 400 to 5500 cm$^{-1}$, preferably from within 4000 to 5500 cm$^{-1}$, most preferably from within 4200 to 4500 cm$^{-1}$ and comparing the attenuation comprises comparing with a predetermined value in said wavenumber range. In some embodiments, the infrared radiation may be recorded in the wavenumber range of 400 to 5500 cm$^{-1}$, preferably in the range 4000 to 5500 cm$^{-1}$, most preferably in the range 4200 to 4500 cm$^{-1}$. In some embodiments, comparing said attenuation of infrared radiation to a predetermined value comprises comparing attenuation of infrared radiation from within the range 4000 cm$^{-1}$ to 4500 cm$^{-1}$, e.g. in the range 4000 cm$^{-1}$ to 4500 cm$^{-1}$. Also recording may be limited to this wavenumber range. It is an advantage of embodiments of the present invention that information from attenuation from within the range 4000 cm$^{-1}$ to 4500 cm$^{-1}$, e.g. in the range 4000 cm$^{-1}$ to 4500 cm$^{-1}$, allows a 100% accurate detection. Said attenuation of infrared radiation then relates to attenuation by integument protein glycation in said integument. It is an advantage of embodiments of the present invention that nail protein glycation can be used as a marker for detecting diabetes. It is an advantage of embodiments of the present invention that the glycation of diabetes target organs such as eye lenses and kidneys can be studied. It is an advantage of embodiments of the present invention that the new marker glucated nail protein reflects the glycation of the majority of the proteins related to target organ damage, e.g. eye lens and kidneys, which can normally undergo deglycation by enzyme fructosamine 3, as opposed to HbA1c which is an another marker that is currently used.

Where said post-translational modification of proteins consists of carbamylation of nail keratins, the method comprises recording of infrared radiation from within the wavenumber range of 4650 to 7700 cm$^{-1}$, e.g. infrared radiation in the wavenumber range of 4650 to 7700 cm$^{-1}$, and comparing the attenuation comprises comparing with a predetermined value in said wavenumber range. In some embodiments, comparing said attenuation of infrared radiation to a predetermined value comprises comparing attenuation of infrared radiation in the range 4650 cm$^{-1}$ to 7700 cm$^{-1}$. Also recording may be limited to this wavenumber range. It is an advantage of embodiments of the present invention that information from attenuation in the range 4650 cm$^{-1}$ to 7700 cm$^{-1}$ allows a 100% accurate detection. Recording and/or comparing infrared radiation may comprise recording and/or comparing from within the wavelength range 1300 nm to 2150 nm, e.g. from within the wavelength range 1300 nm to 1500 nm and/or e.g. from within the range 1525 nm to 1575 nm, and/or e.g. from within the range 1625 nm to 1700 nm and/or e.g. from within the range 1725 nm to 1775 nm and/or e.g. from within the range 1825 nm to 2100 nm, e.g. from within the range 1825 nm to 1950 nm and/or from within the range 1925 nm to 2050 nm and/or from within the range 2050 nm to 2100 nm. Said attenuation of infrared radiation then relates to attenuation by integument protein carbamylation in said integument. It is an advantage of embodiments of the present invention that nail protein carbamylation can be used as a marker for detecting renal insufficiency. It is an advantage of embodiments of the present invention that based on the carbamylation, adverse health effects observed in terminal renal insufficiency such as for example atherosclerosis and anemia can be studied. It is an advantage of embodiments of the present invention that the new marker carbamylated nail protein reflects the carbamylation of the majority of the proteins related to renal insufficiency.

Said protein may be a keratin. It is an advantage of embodiments of the present invention that nail keratin post-translational modification can be used as marker, since keratin is the most abundant nail protein.

The measured post-translational modification of proteins, e.g. glycation or carbamylation, may be reflective of the average post-translational modification of proteins over 0.5 to 9 months prior to said recording, preferably 1 to 6 months. It is an advantage of embodiments of the present invention that the measured results can provide information of the longterm post-translational modification of proteins, i.e. over the post-translational modification of proteins that occurred in the past months, resulting in averaged, thrustworthy, values.

The method may comprise performing Fourier transform infrared spectroscopy. It is an advantage of embodiments of the present invention that an efficient measurement method is obtained that allows fast probing of the required results.

The method may comprise infrared reflection spectroscopy. It is an advantage of embodiments of the present invention that measurements can be performed with little or no sample preparation, since in vivo measurements can be performed. It is furthermore an advantage that the technique is an optical technique and not an invasive technique.

The method may comprise comparing contributions of different spectral bands for deriving a degree of post-translational modification of proteins, e.g. glycation or carbamylation, in a subject. It is an advantage of embodiments of the present invention that the accuracy can even be improved by taking into account different spectral bands.

The method may comprise first removing contaminants from the integument. It is an advantage of embodiments of the present invention that contaminants such as nail polish are first removed, so as to avoid influence on the measured signal and so as to obtain more accurate results.

The predetermined value may be selected as function of a race and/or a gender of the subject. It is an advantage of embodiments of the present invention that interracial differences can be taken into account.

The method may comprise recording attenuation of infrared radiation at different positions on the integument, comparing said attenuation of infrared radiation at different positions to a predetermined value and deriving based thereon a time dependency of the post-translational modification of proteins, e.g. glycation or carbamylation. It is an advantage of embodiments of the present invention that a time evolution of the disease, such as diabetes mellitus or renal insufficiency, can be obtained by measuring at different positions on the nail of a subject along the growth direction of the nails.

In a second aspect, the present invention relates to a system for measuring post-translational modification of proteins in a subject, the system comprising an infrared radiation source, an infrared radiation detector and a data analyser for analysing attenuation of infrared radiation within a predetermined wavenumber range attenuated by an integument of said subject still attached to said subject, by comparing the attenuation with a predetermined value for deriving information regarding post-translational modification of proteins in the integument.

Where said post-translational modification of proteins consists of glycation of nail keratins, the data analyser is adapted for analysing attenuation of infrared radiation from within the wavenumber range of 400 to 5500 cm$^{-1}$, preferably from within 4000 to 5500 cm$^{-1}$, most preferably from within 4200 to 4500 cm$^{-1}$. In particular embodiment, the range is 4000 cm$^{-1}$ to 4500 cm$^{-1}$.

Where said post-translational modification of proteins consists of carbamylation of nail keratins, the data analyser is adapted for analysing attenuation of infrared radiation in the wavenumber range of 4650 to 7700 cm$^{-1}$. The data analyser is adapted for analysing attenuation of infrared radiation from within the wavelength range 1300 nm to 2150 nm, e.g. from within the wavelength range 1300 nm to 1500 nm and/or e.g. from within the range 1525 nm to 1575 nm, and/or e.g. from within the range 1625 nm to 1700 nm and/or e.g. from within the range 1725 nm to 1775 nm and/or e.g. from within the range 1825 nm to 2100 nm, e.g. from within the range 1825 nm to 1950 nm and/or from within the range 1925 nm to 2050 nm and/or from within the range 2050 nm to 2100 nm.

The system may comprise a holder or a positioning means for positioning a finger or tow such that a nail of a subject is positioned with respect to said infrared radiation source and infrared radiation detector.

The system may comprise a Fourier transform infrared spectrometer.

The system may be configured for measuring reflected infrared radiation.

The analyser may be adapted for comparing contributions of different spectral bands for deriving a degree of post-translational modification of proteins, e.g. glycation or carbamylation, in a subject.

The system may be adapted for measuring at different positions on the integument of the subject.

The system may comprise a scanner for scanning with an irradiation beam over a integument of the subject.

In a third aspect, the present invention relates to a post-translational modified integument protein for use in the in vivo diagnosis of anomalous post-translational modification. It is an advantage of embodiments of the present invention that a marker is obtained for in vivo diagnosis of anomalous post-translational modification, being representative of a disease. The post-translational modified integument protein may be a biological marker for said in vivo diagnosis of anomalous post-translational modification. The anomous post-translational modification typically is caused by a disease.

In some embodiments, the invention relates to a glycated integument protein for use in the in vivo diagnosis of anomalous glycemia. It is an advantage of embodiments of the present invention that a marker is obtained for in vivo diagnosis of anomalous glycemia, being representative of diabetes.

The glycated integument protein may be a biological marker for said in vivo diagnosis of anomalous glycemia. The anomalous glycemia is caused by diabetes mellitus.

In some embodiments, the invention relates to a carbamylated integument protein for use in the in vivo diagnosis of anomalous carbamylation. It is an advantage of embodiments of the present invention that a marker is obtained for in vivo diagnosis of anomalous carbamylation, being representative of renal insufficiency.

The carbamylated integument protein may be a biological marker for said in vivo diagnosis of anomalous carbamylation. The anomalous carbamylation is caused by renal insufficiency.

The post-translational modified integument protein may be a keratin.

In a fourth aspect, the present invention relates to the use of a post-translational modified integument protein for in vivo diagnosis of anomalous post-translational modification. The post translational modification may for example be glycation or carbamylation.

The in vivo diagnosis of anomalous post-translational modification may comprise the diagnosis of a disease, such as for example diabetes mellitus or renal insufficiency.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
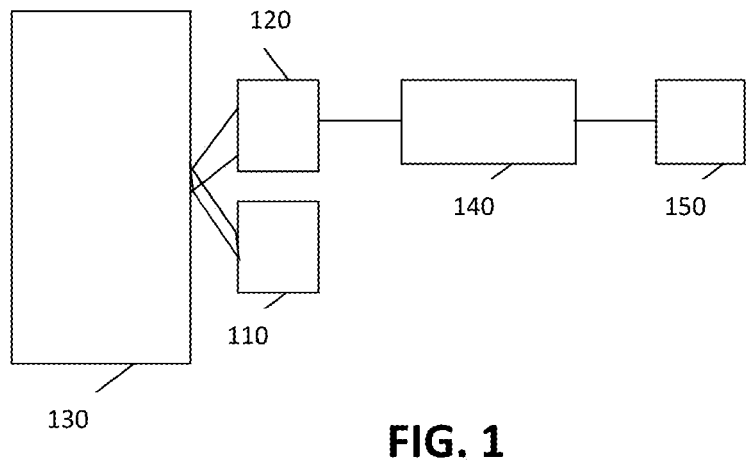
FIG. 1 illustrates a system for measuring post-translational modification of proteins according to an embodiment of the present invention.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Embodiments of the present invention relate to the detection of modifications of proteins in an integument of a human body. In some embodiments, protein glycation in the integument, e.g. nail, is detected, allowing measuring glycation in a subject. The glycation may be an indirect measure for glycamia in the blood. The latter will be discussed intensively below. In other embodiments, protein carbamylation in the integument is detected as a biomarker for carbamylation in renal insufficiency. Carbamylation is a chemical reaction which occurs when the urea isomer, isocyanate, reacts with lysine residues of proteins. As human nails are built up of specific proteins (keratins), carbamylation of keratins can be regarded as an excellent model for assessing carbamylation in a living individual. It nevertheless is to be noted that the present invention is not limited to glycation and carbamylation. In a first aspect, the present invention relates to a method for measuring post-translational modification of proteins in a subject. The method according to embodiments of the present invention may be especially suitable for measuring glycation or carbamylation in a human being, although embodiments of the present invention are not limited thereto and the methods are in principle also applicable to any living creature.

According to embodiments of the present invention, the method comprises recording of infrared radiation within a predetermined wavenumber range, attenuated by an integument of said subject, wherein said integument is still attached to said subject. The method typically may be preceded by irradiation of an integument of the subject with an infrared radiation beam comprising radiation within the predetermined wavenumber range, nevertheless, the step of irradiating could be performed prior to applying the method, so that it is not necessarily a step of the method itself. Alternatively, the method may comprise irradiating the integument of the subject with said infrared radiation. In embodiments of the present invention, the method also comprises comparing said attenuation of infrared radiation to a predetermined value and deriving based thereon information regarding the post-translational modification of proteins. Embodiments of the present invention are especially advantageous for obtaining information regarding diseases, such as for example diabetes mellitus or renal insufficiency, for a subject. According to embodiments of the present invention, in the case of glycation, radiation from within a wavenumber range 400 to 5500 $cm^{-1}$ may be used, advantageously from within a wavenumber range 4000 $cm^{-1}$ to 4500 $cm^{-1}$. According to some other embodiments, in the case of carbamylation, radiation from within a wavenumber range 4650 to 7700 $cm^{-1}$ may be used.

By way of illustration, further optional and standard steps features and advantages of methods according to embodiments of the present invention will further be discussed below. Reference thereby will be made to glycation of proteins as can be used for diabetes mellitus. It will be clear that similar detailed information is valid for other post-translational modification of proteins, such as for example carbamylation, but that corresponding wavenumber ranges, optical components and the like need to be correspondingly adapted mutates mutandis. Such optical components are readily available.

For irradiating the integument, an infrared laser beam may be used, or a focussed irradiation beam may be used. For generating the infrared radiation, an infrared laser may be used, such as for example a near infrared diode laser, but also other infrared radiation sources can be used such as for example a halogen NIR source. The infrared radiation beam spot advantageously has a size such that the irradiation does not exceed the surface of the integument, e.g. the surface of the finger nail. Typical beam spot sizes that may be used correspond with a diameter of up to 3 mm, although embodiments are not limited thereto.

According to embodiments of the present invention, the infrared radiation may be from within the range 4000 to 4500 cm$^{-1}$, since attenuation of infrared radiation in this range by glycated integument proteins is well pronounced.

For irradiating the integument, the subject is typically requested to position the body part comprising the integument in a specific position such that irradiation can be performed in a controllable way. E.g. the subject may be requested to position a finger or tow in a holder, such that the nail can be irradiated in a controlled manner. The holder or positioning means may be such that the integument is positioned below an infrared radiation source and below a detector adjusted for detecting the reflected radiation.

Detection may be performed by detecting a spectrum of the radiation after attenuation by the integument. Alternatively, detection a several specific wavelengths or wavelength ranges also may be performed and may allow to identify glycation of integument proteins. In embodiments, detection techniques that may be used may comprise performing near-infrared (NIR) spectroscopy or may comprise performing Fourier transform infrared spectroscopy, such as for example ATR-FTIR. Both techniques allow for relatively short scan times for a given resolution. It is thus an advantage of embodiments of the present invention that an efficient measurement method is obtained that allows fast probing of the required results.

In embodiments, the method may comprise infrared reflection spectroscopy. In preferred embodiments, the infrared reflection spectroscopy may comprise attenuated total reflection spectroscopy.

Attenuated total reflection (ATR) is a sampling technique which may be used in combination with infrared spectroscopy. It advantageously allows the measurement of samples in solid or liquid state, without further preparation, only requiring the sample to be brought into contact with an ATR crystal. It is thus an advantage of embodiments of the present invention that measurements can be performed with little or no sample preparation, so that in vivo measurements can be performed. It is furthermore an advantage that the technique is an optical technique and not an invasive technique.

As indicated above, the integument of the subject typically may be a nail of a subject. In preferred embodiments, the area of the nail that is probed during the measurement may be the nail plate. Nails typically comprise a large fraction of keratins, such as around 85%, which is one of the markers which may be used for measuring glycation of proteins in the integument, or indirectly glycemia in the blood. As such, it is an advantage of embodiments of the present inventions that the recorded infrared radiation may have been attenuated by a nail, thus typically comprising a relatively strong marker signal. Furthermore, nail plates typically do not contain blood vessels and are metabolically inactive, reducing the possible factors that may influence or interfere with the measured results.

Nevertheless, embodiments are not limited to the use of nails as integument. In some embodiments, the integument also may be the skin of the subject.

In some embodiments, comparing the attenuation of infrared radiation to a predetermined value may comprise comparing attenuation of infrared radiation from within the range 4000 cm$^{-1}$ to 4500 cm$^{-1}$. It has been found that using this specific infrared radiation results in the possibility of obtaining very accurate measurements of glycation and thus in very accurate detection of diabetes mellitus. Comparison of the attenuation may for example be performed using a predetermined algorithm or using look up tables. It may be performed automatically upon input and/or in an automated way, e.g. using a processor programmed for performing such a comparison. The comparison provides comparison results that can be provided as output, e.g. displayed. The comparison results may provide an indication of whether the measured level is above or below a certain threshold. Whereas based on the comparison results an indication could be given whether or not a subject suffers from diabetes mellitus, such a diagnosis in some embodiments is not part of the method, and may be performed separately, i.e. outside the method, by a medically trained person. The diagnosis thus may be not a part of the method.

In some embodiments, the predetermined value used for comparing may be determined based on additional characteristics of the subject such as race and/or gender. Consequently, such information may be used as input and may be prompted for by the processor. That information, in combination with the obtained measurement results, then may result in the comparison results.

It is an advantage of embodiments of the present invention that the glycation of diabetes target organs such as eye lenses and kidneys can be studied.

It is an advantage of embodiments of the present invention that the new glycated integument protein marker reflects the glycation of the majority of the proteins related to target organ damage, e.g. eye lens and kidneys, which can normally undergo deglycation by enzyme fructosamine 3, as opposed to HbA1c which is an another marker that is currently used.

In embodiments, said protein may be a keratin.

It is an advantage of embodiments of the present invention that integument keratin glycation can be used as marker, since, particularly in nails, keratin is an abundant integument protein.

According to some embodiments, the method provides results that are representative of an average glycemia, e.g. of glycemia that occurred over a period with a length between 0, 5 months and 9 months, e.g. over a period with a length between 1 and 6 months. It is an advantage of embodiments of the present invention that the measured results can provide information of the longterm glycemia, i.e. over the glycemia that occurred in the past months, resulting in averaged, thrustworthy, values.

According to some embodiments, the measurements are performed such that a time evolution of glycation of the integument protein can be measured and followed. The method may for example comprise recording attenuation of infrared radiation at different positions on the integument, comparing said attenuation of infrared radiation at different positions to a predetermined value and deriving based thereon a time dependency of the glycemia. If for example measuring at different positions along the growth direction of a nail can be performed, this allows to obtain results representative of the time evolution of glycation. For example, the tip of the nail plate is typically reflective of earlier glycation, such as the glycation 6 to 9 months prior to the measurement, while the nail plate region closer to the nail matrix is typically reflective of more recent glycation, such as the glycation 0.5 to 1 month prior to the measurement. Measurement at different positions of the nail may thus be used to build a time evolution of glycation, for example over the last 6 to 9 months. Furthermore, by sampling a larger or smaller part of the nail, an average value for the glycation over a larger or smaller window of time may be obtained; for example, by sampling the entire nail plate an average value of glycation over the last 6 to 9 months may be obtained.

In some embodiments, the method may comprise first removing contaminants from the integument. The latter may for example be performed using conventional cleaning products. It is an advantage of embodiments of the present invention that contaminants such as nail polish are first removed, so as to avoid influence on the measured signal and so as to obtain more accurate results.

In a second aspect, the present invention relates to a system for measuring post-translational modification of proteins, such as for example glycation or carbamylation, in a subject, the system comprising an infrared radiation source, an infrared radiation detector and a processor, e.g. data analyser, for analysing attenuation of infrared radiation within a predetermined wavenumber range attenuated by an integument of said subject still attached to said subject, by comparing the attenuation with a predetermined value for deriving information regarding the post-translational modification of proteins. According to embodiments of the present invention, in the case of glycation, a data analyser for analysing radiation from within a wavenumber range 400 to 5500 $cm^{-1}$ may be used, advantageously from within a wavenumber range 4000 $cm^{-1}$ to 4500 $cm^{-1}$. According to some other embodiments, in the case of carbamylation, a data analyser for analysing radiation form within a wavenumber range 4650 to 7700 $cm^{-1}$ may be used. The system may be especially suitable for performing a method for measuring post-translational modification of proteins as described in the first aspect.

By way of illustration, a system according to an embodiment of the present invention is schematically represented in FIG. 1. Again, the system described is particularly suitable for measuring glycation, but it will be understood that by adjusting the wavenumber range and the corresponding optical components, a corresponding system is described for measuring of other post-translational modifications of proteins, such systems herewith thus also being described. FIG. 1 shows a system 100 for measuring glycemia. The system 100 comprises a radiation source 110, a detector 120 configured for detecting infrared radiation from the radiation source 110 after it has been attenuated by an integument of a subject, and a holder or positioning means 130 for positioning an integument of a subject with respect to the radiation source 110 and the detector 120. The holder or positioning means 130 may for example be suited for holding a hand or a finger or a foot or a tow in a position such that the nail of a finger or tow is accurately positioned for performing measurements. Alternatively, the positioning means may correspond with a positioning means for the system such that it can be mounted to a hand, finger, foot or tow and such that the nail of a finger or tow is accurately positioned with respect to the system, such that measurements can be performed. The system furthermore comprises a processing means or processor 140 for processing the detected attenuated radiation received at the detector 120. The processor thereby is adapted for comparing the obtained measurement results with predetermined values. This comparison or a result based thereof may be outputted through an output means 150. As indicated in the first aspect, the radiation source and detector may be adapted for generating infrared radiation from within the range 4000 $cm^{-1}$ to 4500 $cm^{-1}$, and/or the processor may be adapted for processing infrared radiation in this frequency range. The detector may be a Fourier transform infrared spectrometer, a detector adapted for measuring reflected IR radiation, a detector configured for performing attenuated total reflection Fourier transform infrared spectroscopy (ATR-FTIR).

In embodiments, the processor may be adapted for comparing contributions of different spectral bands for deriving a degree of glycemia in a subject.

In some embodiments, the system may be adapted for measuring at different positions on the integument of the subject, e.g. by providing a scanning movement of the irradiation beam over the integument of the subject. In embodiments, the system thus may comprise a scanner for scanning with an irradiation beam over an integument of the subject.

Further features and advantages of the system may correspond with the features and advantage described for the corresponding method in the first aspect.

In a third aspect, the present invention relates to a post-translational modified integument protein, e.g. glycated integument protein or carbamylated integument protein, for use in the in vivo diagnosis of anomalous post-translational modification of proteins. It is an advantage of embodiments of the present invention that a marker is obtained for the in vivo diagnosis of anomalous post-translational modification of proteins. The anomalous post-translational modification of proteins is typically representative of a form of hyperglycemia, such as caused by diabetes mellitus, or a form of hypoglycemia or of a form of hypercarbamylation. In other cases, the anomalous post-translational modification of proteins may be in the form of a varying or irregular post-translational modification over time. In embodiments, the post-translational modified integument protein may be a biological marker for said in vivo diagnosis of anomalous post-translational modification of proteins. In embodiments, said anomalous post-translational modification of proteins may be caused by diabetes mellitus. In embodiments, the post-translational modified integument protein may be a keratin. The integument may be a nail.

In a fourth aspect, the present invention relates to the use of a post-translational modified integument protein for in vivo diagnosis of anomalous post-translational modification of proteins. In embodiments, said in vivo diagnosis of anomalous post-translational modification of proteins may comprise the diagnosis of a disease such as for example diabetes mellitus or renal insufficiency.

The invention will now be described by a detailed description of several embodiments of the invention. It is clear that other embodiments of the invention can be configured according to the knowledge of the person skilled in the art without departing from the true technical teaching of the invention, the invention being limited only by the terms of the appended claims.

Example: Infrared Spectroscopy on Nails of Patients with Diabetes Mellitus and a Control Group Near infrared spectra were taken of the nail plate of 5 patients diagnosed with diabetes mellitus and 25 people in a control group, all belonging to the same race.

Figure 2A:
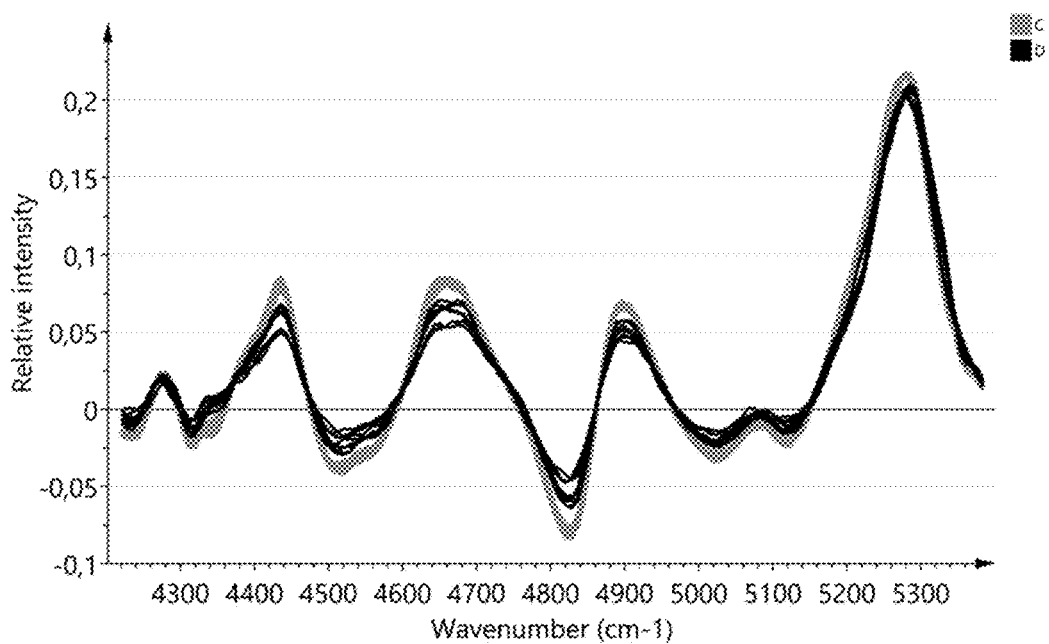
FIG. 2a to 4b show near infrared spectra (a) and analysis of the spectra (b) according to an example of the present invention for different wavenumber ranges.
Figure 2B:
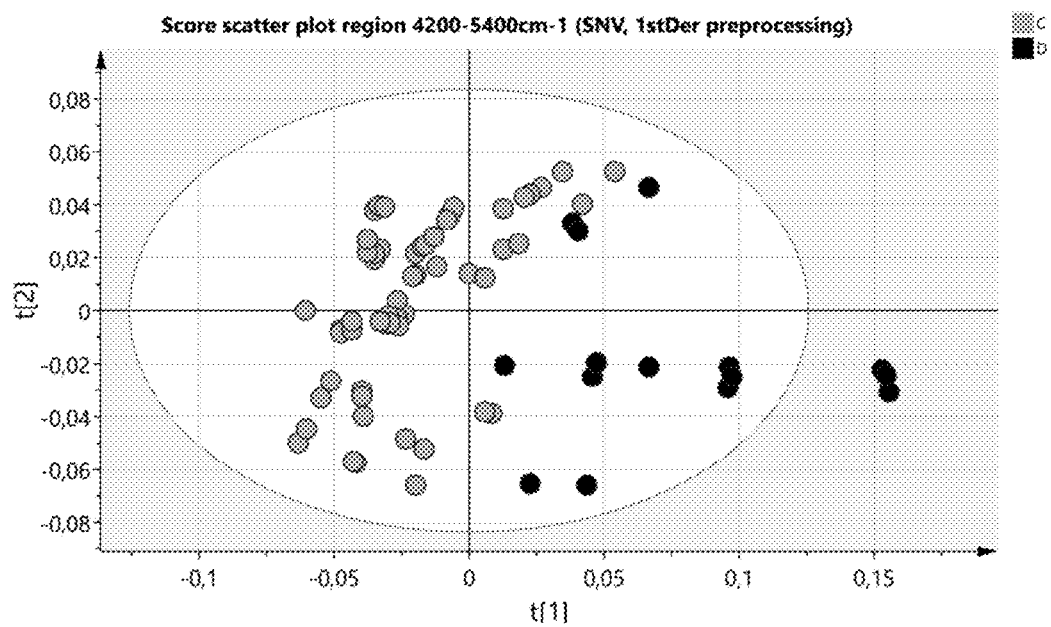

The NIR spectra were taken in the wavenumber range of 4200 cm$^{-1}$–5400 cm$^{-1}$ and plotted in FIG. 2a. As can be seen, the spectra between both groups are clearly distinguished. To better quantify this spectral differentiation, for each measurement the spectra were analysed by setting out, in FIG. 2b, the standard normal variate (SNV). A fairly good separation between, on the one hand, the data points corresponding to the diabetes mellitus group and, on the other hand, the control group can be observed.

Figure 3A:
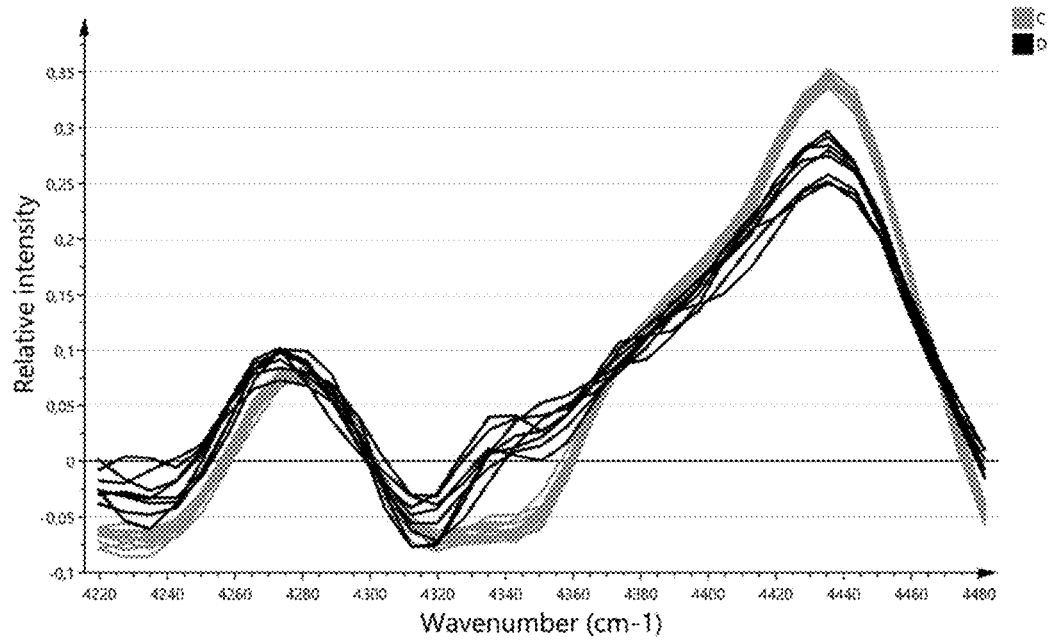
Figure 3B:
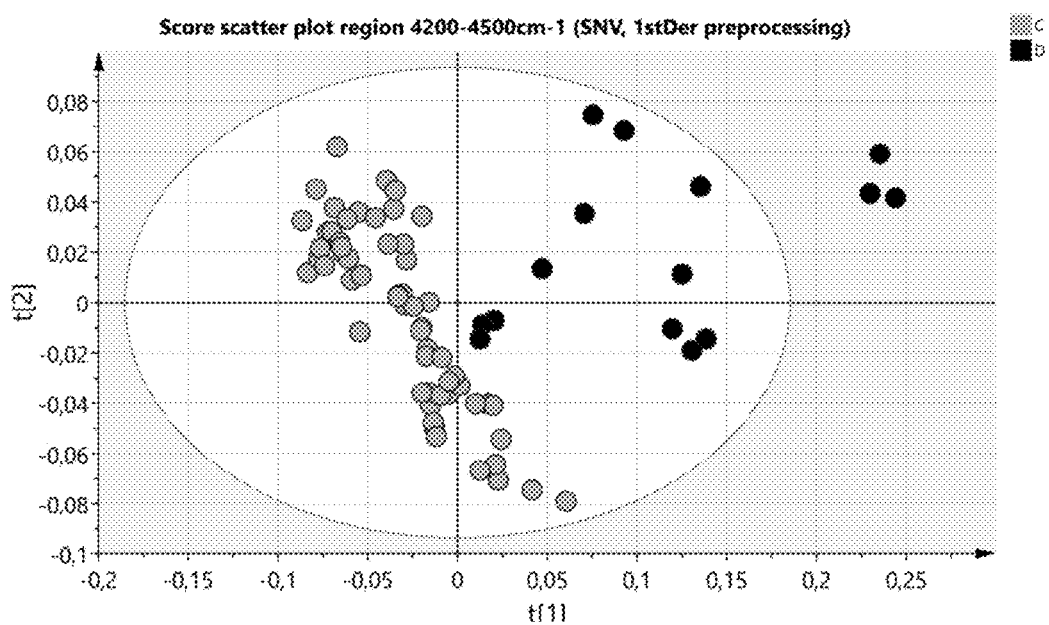

In order to further improve the separation, the spectral range was reduced to 4200-4500 cm$^{-1}$ and the resulting spectra are shown in FIG. 3a. Again, for each measurement, the spectra were analysed by setting out, in FIG. 3b, the SNV. It could be observed that the separation between both groups is further improved. Furthermore, it was possible to 100% accurately predict to which group a given sample belonged, after the evaluation model used was trained using a set of training data.

Figure 4A:
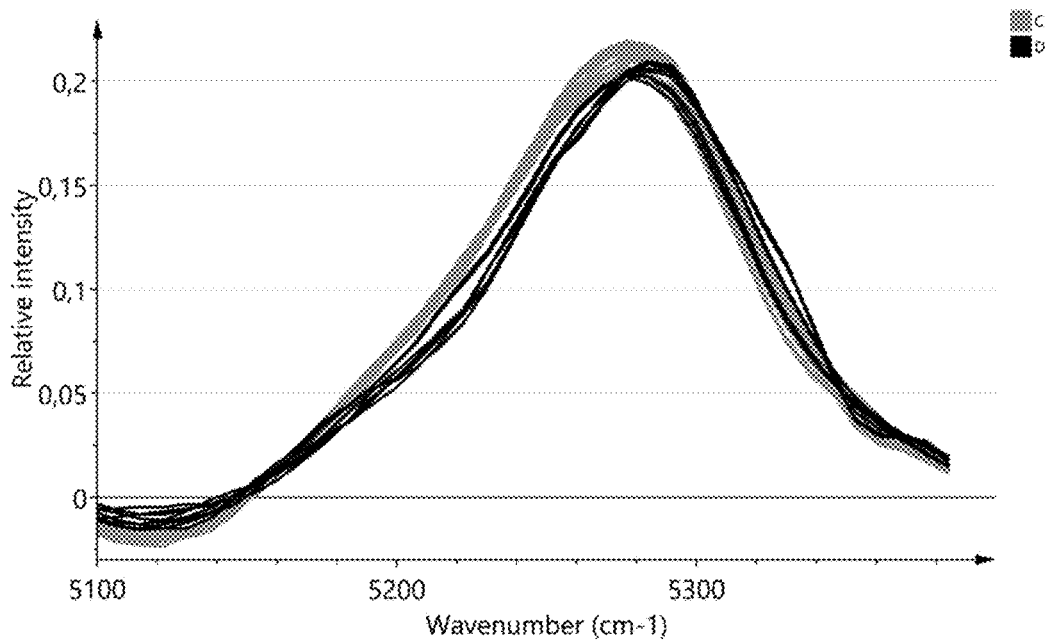
Figure 4B:
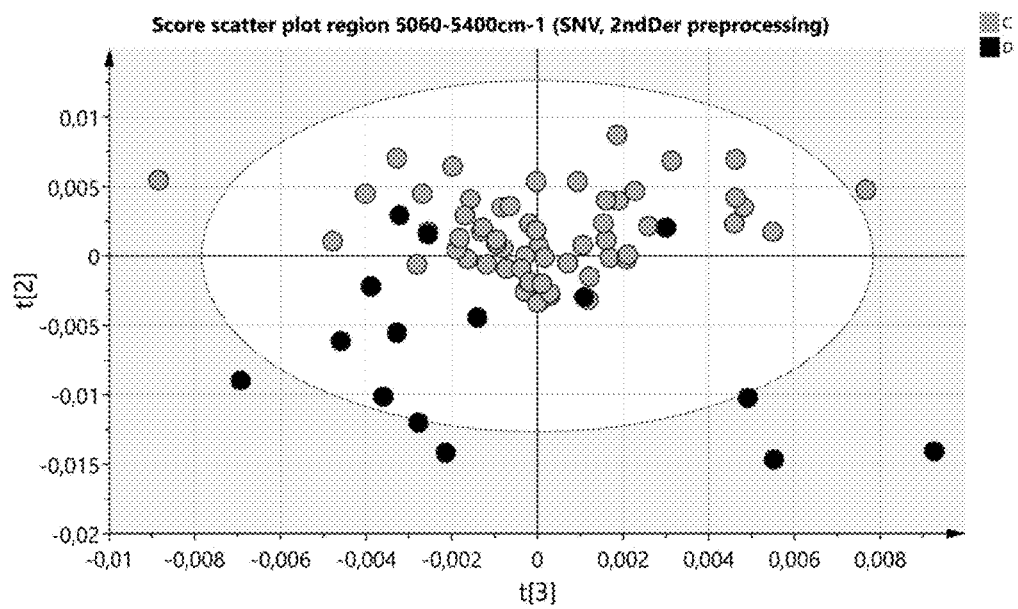

Similarly, the spectral range was also limited to 5060-5400 cm$^{-1}$ and the corresponding spectra are shown in FIG. 4a. Again, for each measurement, the spectra were analysed in FIG. 4b, whereby a second derivative was analysed. However, in this case the separation was not improved and no 100% conclusive predictions could be performed, similar as for evaluation of the first derivative (not shown).

Example: Monitoring Glycation During Treatment

Figure 5:
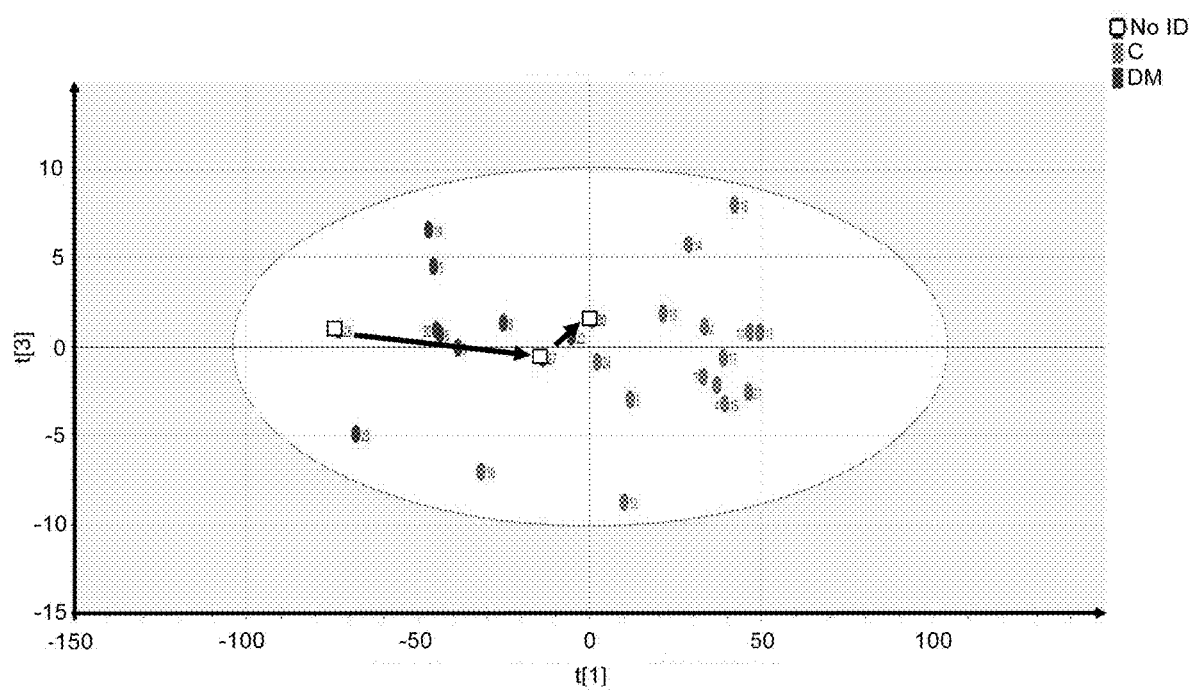
FIG. 5 illustrates the change in glycation over time during treatment, according to an embodiment of the present invention.

Near infrared spectra were taken of the nail plate of patients as function of treatment of the patient. As glucose diffuses from the capillary network into the finger nail and the nail grows in function of time, it is possible to observe fluctuations of NIR-spectra due to changing diffusion of glucose from the blood to the nail. So this makes it possible to observe an improvement of the data when a diabetic patient is treated in function of time. In FIG. 5, diabetes type 2 patients are monitored during treatment with metformin (3×850 mg daily). Again the standard normal variate value is given of the 1$^{st}$ derivative of the spectrum. The results for a specific patient (open square) are discussed in detail, whereby reference values for a control group (C) and for a diabetes group (DM) are also shown. Measurement number 26 was the first measurement at the start of the treatment and is located in the diabetic (blue) group. Measurement number 27 is the second measurement, a few weeks later during which the patient was treated. It can be seen that the second measurement is progressing towards the control group. This means that the situation for the patient is improving (mean glycemia has dropped from 279 mg/dl to 105 mg/dl). Measurement number 30 is the third measurement, again a few weeks later after the second measurement. This plot (data collected over a 5 weeks interval) nicely illustrates the use of non-invasive NIR monitoring enables to assess the glycemic control.

Figure 6A:
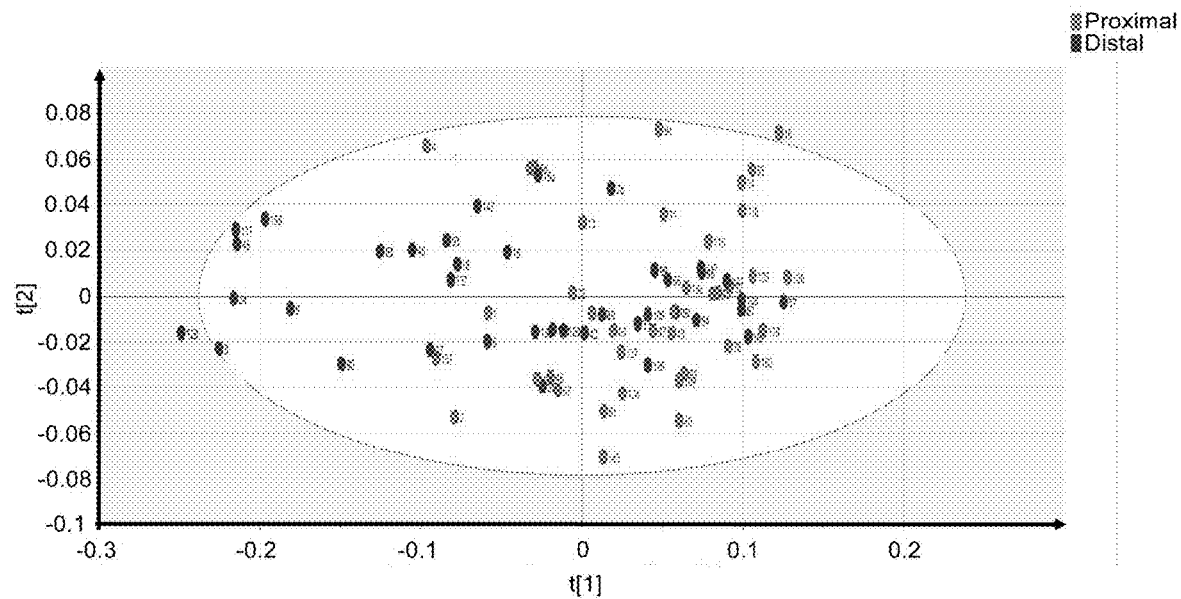
FIGS. 6a and 6b illustrates the difference in glycation between the proximal zone and the distal zone of the finger nail, for a control group (FIG. 6a) and a diabetic group (FIG. 6b), illustrating features of an embodiment according to the present invention.
Figure 6B:
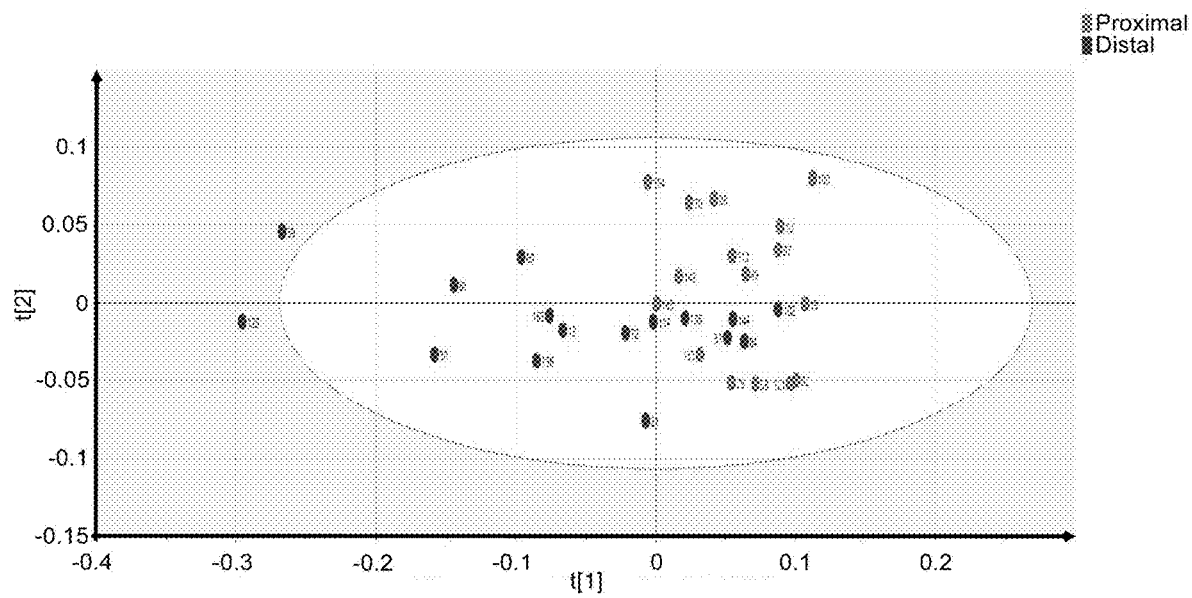

Example: Evaluating Time Evolution Based on NIR Measurements on Different Zones of the Finger Nail Different zones on the finger nails were measured using NIR spectra in a spectral range 1460 nm to 1630 nm for both a control group and a diabetic group. If there is a difference between the proximal zone and the distal zone of the finger nail, this indicates that there is accumulation of glucose in the nail as the nail grows. The results for the control group are shown in FIG. 6a whereas the results for the diabetic group are shown in FIG. 6b. In both cases, there are roughly two groups visible in the scores plot. The distal measurements are more to the left and the proximal measurements more to the right. However there is still some overlap between the two areas due to variations of the glucose concentrations in the finger nails of different test persons.

Example: Infrared Spectroscopy on Nails of Patients with Renal Insufficiency and a Control Group Near infrared spectra were taken of the nail plate of a number of patients presenting with terminal renal insufficiency and a number of people in a control group, all belong to the same race.

Figure 7A:
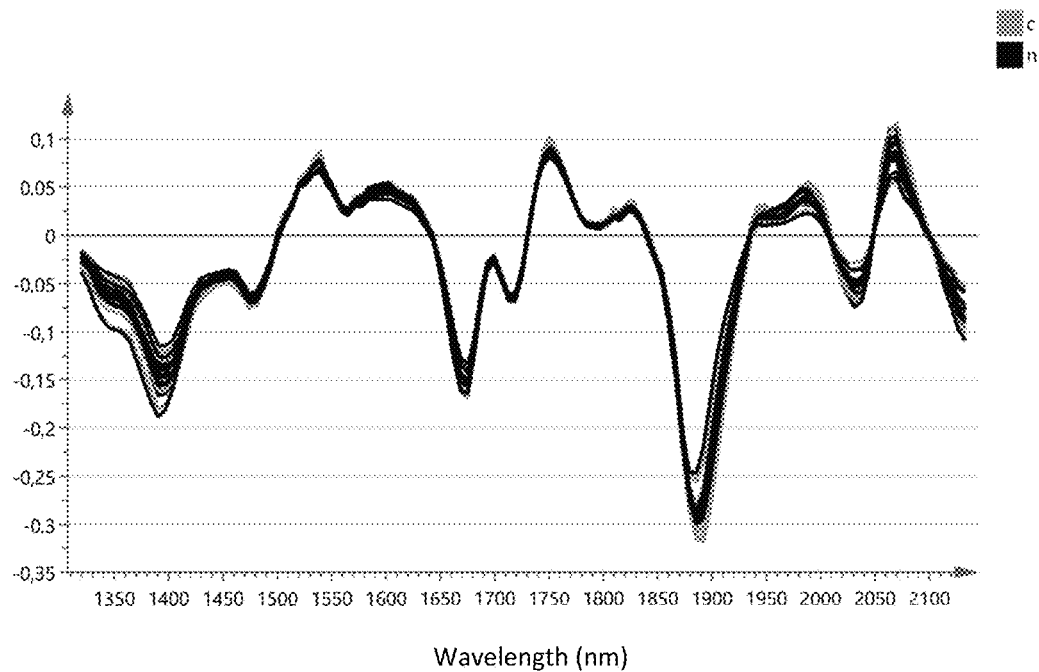
FIGS. 7a and 7b illustrate infrared spectra (FIG. 7a) and analysis of the spectra (FIG. 7b) for carbamylation, according to an embodiment of the present invention.
Figure 7B:
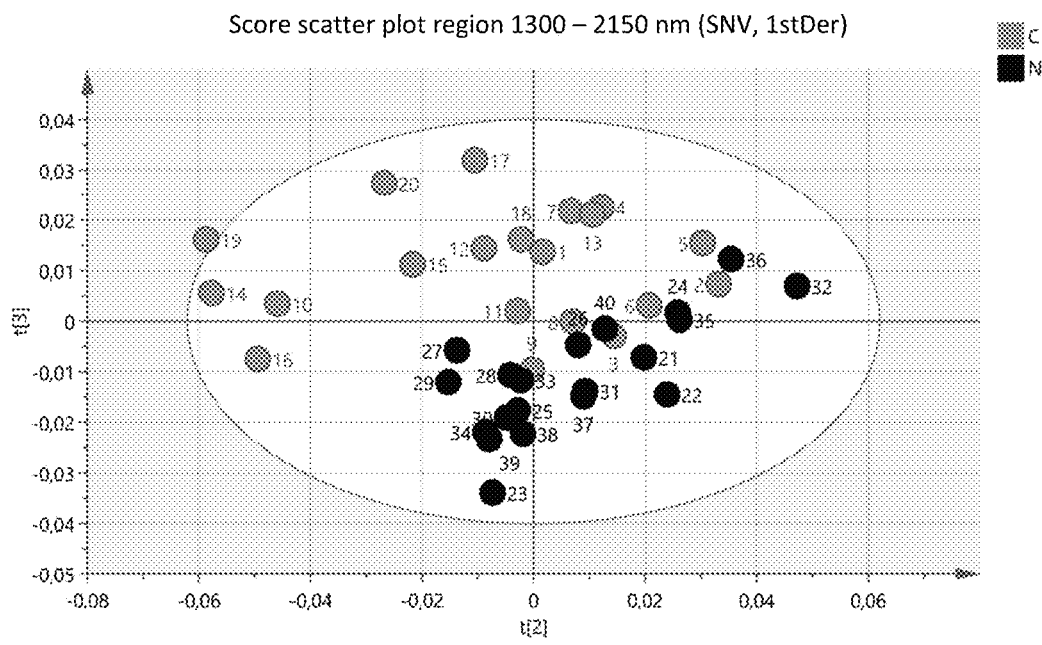

The NIR spectra were taken in the wavelength range 1300 nm to 2150 nm. As can be seen in FIG. 7a, spectral differences can be noted between spectra for people in the control group (c) and people suffering from renal insufficiency (N). To better quantify this spectral differentiation, a principal components analysis of the spectra was performed and the spectra were analysed by setting out, in FIG. 7b, the standard normal variate (SNV). It can be seen that there is a clear distinction between people of the control group (C) and people suffering from renal insufficiency (N). It can be seen that near infrared spectroscopy on human nails offers an excellent tool for a non-invasive assessment of carbamylation.

It is to be understood that although preferred embodiments, specific constructions and configurations, as well as materials, have been discussed herein for devices according to the present invention, various changes or modifications in form and detail may be made without departing from the scope and technical teachings of this invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A method for measuring post-translational modification of proteins in a subject, the method comprising:
    measuring and recording of infrared radiation within a predetermined wavenumber range on a nail plate of the subject, wherein said nail plate is still attached to said subject, the infrared radiation being attenuated by nail plate protein glycation in the nail plate;
    comparing said attenuation of infrared radiation to a predetermined value for deriving information regarding post-translational modification of proteins in the nail plate;
    wherein said comparing comprises comparing a contribution of different spectral bands within a range of 4000 cm$^{-1}$ to 4500 cm$^{-1}$; and
    deriving a degree of glycemia in the subject based on said comparison of the contribution of different spectral bands within the range of 4000 cm$^{-1}$ to 4500 cm$^{-1}$,
    wherein said attenuation of infrared radiation comprises attenuation by post-translational modified integument protein in said nail, said protein being a keratin.

2. The method according to claim 1, wherein the method comprises performing any of near infrared spectroscopy, Fourier transform infrared spectroscopy or infrared reflection spectroscopy.

3. The method according to claim 1, wherein the method comprises recording attenuation of infrared radiation at different positions on the nail plate, comparing said attenuation of infrared radiation at different positions to a predetermined value and deriving based thereon a time dependency of the post-translational modification of proteins.

4. The method according to claim 1, wherein the method comprises selecting said predetermined value as function of race or gender of the subject.

5. A system for measuring post-translational modification of proteins in a subject, the system comprising an infrared radiation source, an infrared radiation detector and a data analyser for analysing attenuation of infrared radiation within a predetermined wavenumber range attenuated by a nail plate of said subject still attached to said subject, the infrared radiation being attenuated by nail plate protein glycation in the nail plate, by comparing the attenuation with a predetermined value for deriving information regarding post-translational modification of proteins in the nail plate;
  wherein the analyser is configured to compare a contribution of different spectral bands within a range of $4000\ cm^{-1}$ to $4500\ cm^{-1}$; and
  deriving a degree of glycemia in the subject based on said comparison of the contribution of different spectral bands within the range of $4000\ cm^{-1}$ to $4500\ cm^{-1}$, and
  wherein said system comprises a holder for positioning a finger or toe such that a nail of a subject is positioned with respect to said infrared radiation source and infrared radiation detector.

6. The system according to claim 5, wherein the system is adapted for measuring at different positions on the nail plate of the subject.

7. The system according to claim 5,
  wherein said post-translational modification of proteins consists of glycation of nail keratins, the data analyser being adapted for analysing attenuation of infrared radiation from within the wavenumber range of 400 to $5500\ cm^{-1}$.

8. A post-translation modified integument protein for use in in vivo diagnosis of anomalous post-translation modification of proteins comprising the method of claim 1.

9. The post-translation modified integument protein according to claim 8, the post-translation modified integument protein being a biological marker for said in vivo diagnosis of anomalous post-translation modification of proteins.

10. The post-translation modified integument protein according to claim 8, the post-translation modified integument protein being a keratin or a glycated integument protein.

11. Use of the post-translation modified integument protein according to claim 8 for the in vivo diagnosis of a disease.

12. The use of the post-translation modified integument protein according to claim 11, wherein the post-translation modified integument protein is a glycated protein and wherein said in vivo diagnosis comprises the diagnosis of diabetes mellitus.

13. A method for measuring post-translational modification of proteins in a subject, the method comprising:
  measuring and recording of infrared radiation within a predetermined wavenumber range on a nail plate of the subject, wherein said nail plate is still attached to said subject, the infrared radiation being attenuated by nail plate protein glycation in the nail plate;
  comparing said attenuation of infrared radiation to a predetermined value for deriving information regarding post-translational modification of proteins in the nail plate;
  wherein said comparing comprises comparing a contribution of different spectral bands within a range of $4000\ cm^{-1}$ to $4500\ cm^{-1}$; and
  deriving a degree of glycemia in the subject based on said comparison of the contribution of different spectral bands within the range of $4000\ cm^{-1}$ to $4500\ cm^{-1}$.

* * * * *